US012458402B2

(12) United States Patent
Stehr et al.

(10) Patent No.: US 12,458,402 B2
(45) Date of Patent: Nov. 4, 2025

(54) DEVICE, BRUSH, RANGE AND METHOD FOR REMOVING ACARINE PARASITES BY ROTATION

(71) Applicants: Malipano GmbH, Bayreuth (DE); Hecht International GmbH, Burgoberbach (DE)

(72) Inventors: Horst Stehr, Bayreuth (DE); Isabell Kerstin Stehr, Bayreuth (DE)

(73) Assignees: malipano GmbH, Bayreuth (DE); hecht international GmbH, Burgoberbach (DE)

( * ) Notice: Subject to any disclaimer, the term of this patent is extended or adjusted under 35 U.S.C. 154(b) by 1058 days.

(21) Appl. No.: 17/500,078

(22) Filed: Oct. 13, 2021

(65) Prior Publication Data

US 2022/0031361 A1 Feb. 3, 2022

Related U.S. Application Data

(63) Continuation of application No. PCT/EP2020/060080, filed on Apr. 8, 2020.

(30) Foreign Application Priority Data

Apr. 13, 2019 (DE) ......................... 102019002743.4
Apr. 3, 2020 (DE) ......................... 202020101827.2

(51) Int. Cl.
*A61B 17/50* (2006.01)

(52) U.S. Cl.
CPC ........ *A61B 17/50* (2013.01); *A61B 2017/505* (2013.01)

(58) Field of Classification Search
CPC .............. A61B 17/50; A61B 2017/505; A46B 2200/102; A46B 13/008
See application file for complete search history.

(56) References Cited

U.S. PATENT DOCUMENTS

| | | | |
|---|---|---|---|
| 4,865,482 | A | 9/1989 | Van Landingham |
| 6,106,041 | A | 8/2000 | Eckhardt |
| 7,699,869 | B2 | 4/2010 | Meinhold et al. |
| 8,123,761 | B2 | 2/2012 | Herweijer et al. |
| 9,107,486 | B2 | 8/2015 | Brewer et al. |
| 2004/0134002 | A1 | 7/2004 | Zimmer |

(Continued)

FOREIGN PATENT DOCUMENTS

| | | | |
|---|---|---|---|
| CA | 2790059 | A1 | 3/2013 |
| CN | 1882267 | A | 12/2006 |

(Continued)

*Primary Examiner* — Anh T Dang
(74) *Attorney, Agent, or Firm* — Laurence A. Greenberg; Werner H. Stemer; Ralph E. Locher

(57) ABSTRACT

A device for moving an acarine parasite which has penetrated the skin of a host, in particular a tick, has a drive, in particular an electromotive drive, which is received in a housing, and an attachment, which has an interface on the drive side and can be rotated about a rotational axis and which contains a number of fibers arranged in the form of bristles as a fiber assembly. The fiber assembly has a recess, preferably a coaxial recess, in particular a conical or truncated conical or parabolic recess, and a fiber wreath assembly, which is formed by the fibers at the free ends thereof along the circumference of the recess and which has at least one fiber wreath with a wreath width which is greater than or equal to 0.3 mm, preferably 0.8±0.4.

19 Claims, 5 Drawing Sheets

(56) References Cited

U.S. PATENT DOCUMENTS

| | | | |
|---|---|---|---|
| 2013/0324802 | A1 | 12/2013 | Makosky et al. |
| 2015/0065927 | A1 | 3/2015 | Brewer et al. |
| 2015/0182415 | A1 | 7/2015 | Olkowski et al. |
| 2017/0119143 | A1 | 5/2017 | Steiner |
| 2018/0098615 | A1 | 4/2018 | George et al. |

FOREIGN PATENT DOCUMENTS

| | | | |
|---|---|---|---|
| CN | 101083945 | A | 12/2007 |
| CN | 105338857 | A | 2/2016 |
| CN | 205359356 | U | 7/2016 |
| CN | 205830744 | U | 12/2016 |
| CN | 106264363 | A | 1/2017 |
| CN | 206325031 | U | 7/2017 |
| CN | 107135976 | A | 9/2017 |
| CN | 108078464 | A | 5/2018 |
| CN | 207613694 | U | 7/2018 |
| CN | 108450351 | A | 8/2018 |
| CN | 108882791 | A | 11/2018 |
| CN | 108968748 | A | 12/2018 |
| CN | 108991713 | A | 12/2018 |
| CN | 109008175 | A | 12/2018 |
| CN | 109077435 | A | 12/2018 |
| CN | 208318024 | U | 1/2019 |
| CN | 208426030 | U | 1/2019 |
| DE | 19827651 | C1 | 1/2000 |
| DE | 10102192 | A1 | 11/2002 |
| DE | 202006004243 | U1 | 6/2006 |
| DE | 202013006700 | U1 | 9/2013 |
| DE | 202014010570 | U1 | 12/2015 |
| EP | 1036522 | A2 | 9/2000 |
| EP | 1384418 | A1 | 1/2004 |
| EP | 1658012 | B1 | 3/2007 |
| EP | 2886098 | A1 | 6/2015 |
| EP | 3607903 | A1 | 2/2020 |
| JP | 2002186374 | A | 7/2002 |
| JP | 2005110966 | A | 4/2005 |
| KR | 1020050002114 | A | 1/2005 |
| KR | 10-20090110151 | A | 10/2009 |
| KR | 20090110151 | A | 10/2009 |
| KR | 101303781 | B1 | 9/2013 |

DEVICE, BRUSH, RANGE AND METHOD FOR REMOVING ACARINE PARASITES BY ROTATION

CROSS-REFERENCE TO RELATED APPLICATION

This application is a continuation, under 35 U.S.C. § 120, of copending International Patent Application PCT/EP2020/060080, filed Apr. 8, 2020, which designated the United States; this application also claims the priority, under 35 U.S.C. § 119, of German Patent Application DE 10 2019 002 743.4, filed Apr. 13, 2019 and DE 20 2020 101 827.2, filed Apr. 3, 2020; the prior applications are herewith incorporated by reference in their entirety.

FIELD AND BACKGROUND OF THE INVENTION

The invention relates to a device for removing an acarine parasite that has penetrated into a host's skin. The device is especially intended and set up to remove a tick from the skin of humans or animals.

German patent DE 198 276 51 C1, corresponding to U.S. Pat. No. 6,106,041, discloses an apparatus for removing ticks by means of gripper arms produced by injection molding from elastic polymer, joined to one another in one piece via a support strut at a point between two grab handles and gripper jaws that project out of a housing. By virtue of the intrinsic elasticity of the gripper arms that act in the manner of plastic tweezers, the gripper jaws are pushed together with a defined closing force when the device is not being operated.

European patent EP 1 658 012 B1, corresponding to U.S. Pat. No. 7,699,869, discloses an apparatus for removing parasites or ticks from the skin of humans or animals, having a spreading device for spreading a gripper tool which, in the unspread state, encloses an essentially closed cavity for accommodating the parasite or tick. A compression device that acts in axial direction serves to actuate the gripper tool and a rotating device for rotating the gripper tool.

SUMMARY OF THE INVENTION

It is an object of the invention to specify a particularly suitable device for removing an acarine parasite that has penetrated into a host's skin, especially a tick. More particularly, the removal of ticks from a host's skin should be enabled without endangering the host's health. Furthermore, a brush attachment particularly suitable for the removal of acarine parasites, especially ticks, is to be specified. In addition, with regard to various sizes of acarine parasites, especially larvae, nymphs and/or ticks, a suitable range comprising suitable brush attachments is to be provided.

This object is achieved in accordance with the invention with regard to the device by the features of the independent device claim, and with regard to the brush attachment by the features of the independent brush attachment claim, and with regard to the range by the features of the independent range claim.

The device provided and set up for removal of an acarine parasite that has penetrated into a host's skin, especially a tick, has a drive accommodated in a housing and an attachment, also referred to hereinafter as brush attachment, having a multitude of fibers in a brush-like or bristle-like arrangement, referred to hereinafter as fiber arrangement. The housing is appropriately cylindrical. It suitably contains a handle in the form of a grip surface and/or a recessed grip for safe handling of the device.

What is also understood by "attachment" is a holding device, especially in sleeve form, for the fibers in a brush-like or bristle-like arrangement. "Fiber" is understood to mean a filament-like elongated body like a hair.

The fiber arrangement has a recess, preferably a coaxial recess, especially in conical or frustoconical form. In other words, the fiber arrangement, proceeding from its free fiber ends, has a depression that narrows axially toward the drive-side interface of the brush attachment for accommodating the body of a parasite or tick. The recess, which is practically effective in the manner of a hood, preferably takes the form of an (elliptical) paraboloid. A paraboloid-shaped recess is matched in a particularly suitable manner to the typical shape of a tick's body.

The fibers of the fiber arrangement of the brush attachment, at the free ends of the fibers along the circumference of the recess, form a fiber ring arrangement with at least one fiber ring, where the ring width of the fiber ring arrangement is not less than 0.3 mm, preferably (0.8±0.4) mm. The ring width is half the difference between the outer dimension (external diameter) and the inner dimension (inner diameter) of the fiber ring arrangement at the opening (mouth) of the recess at the free ends of the fibers. The ring width may be provided by a single, radially outer fiber ring or by a number of radially outer fiber rings. More preferably, the fiber ring arrangement is composed of two (radially outer) fiber rings, especially of identical (axial) fiber or fiber ring length, where the ring width of this fiber ring arrangement is preferably 0.6 mm to 1.4 mm, more preferably 0.7 mm to 1.2 mm.

The brush attachment has, on the drive side, an interface for coupling onto the drive which is accessible especially at an end face of the housing. The brush attachment that can be coupled to the drive, meaning that it is releasably connected thereto and is especially exchangeable, can be rotor-driven about an axis of rotation and, for this purpose, has the (mechanical) interface on the drive side.

In a particularly advantageous configuration, the brush attachment, i.e. the attachment with the fibers, is a one-piece (one-part, monolithic) injection molding, especially a one-component injection molding, preferably made of plastic. The brush attachment produced in this way is particularly effective for removal of ticks from a host's skin and is additionally producible inexpensively.

The drive suitably has an electric motor and a reduction gear. Appropriately, the drive has a drive shaft to which the brush attachment can be fitted in a fixed manner at the end of the shaft. The drive shaft is suitably accessible at an end face of the housing, where it forms the coupling site for the brush attachment. The reduction is preferably adjusted such that the speed of the brush attachment is between 30 rpm (revolutions per minute) and 150 rpm, especially (70±20) rpm, preferably (60±10) rpm, or especially (100±30) rpm, preferably (120±10) rpm.

The invention proceeds from the recognition that, firstly, owing to the fact that a tick, in its life-cycle, often leaves the puncture site in a host's skin and for this purpose necessarily removes the puncture or suction apparatus (hypostome) from the host's skin, there must be a reliable way of stimulating the tick to do so. Secondly, in the course of removal, there should be a reliable avoidance of damage to or breakoff of the body of the tick as it exits from the host's skin, especially since, in practical terms, such damage or such tick breakage risks the transfer of pathogens (bacteria or viruses). This is true regardless of the body size or growth stage from the larva (0.3 mm to 0.8 mm) through the nymph (0.8 mm to 2.0 mm) to the tick (from about 2.5 mm).

The invention therefore proceeds from the consideration that injury to the tick or tearing-off (tick breakoff), especially of its tick body that projects out of the host's skin, is reliably avoided when the tick is not compressed (squeezed) at any point in the course of its removal, i.e. no compressive, tensile and/or lifting force is exerted on the tick, which is virtually unavoidable by means of conventional gripper, loop or lever mechanisms. This can be achieved when the tick is merely rotated about its axis without exerting pressure in the course of removal from the host's skin.

Corresponding studies by means of the device have shown that the tick—even in the case of a tick larva from 0.3 mm—after just a few rotating movements removes its puncturing/sucking apparatus from the host's skin and leaves the puncture site. This is assisted particularly advantageously by the recess provided in the brush attachment and positioned above the tick's body, such that the tick, while it is being rotated with the brush attachment, is virtually not compressed or squeezed. It is acknowledged that the grip reflex of the tick's legs is probably also utilized here. It is at least the case that these hang with the fibers, especially the fiber rings, of the brush attachment of the device, and the tick is repeatedly turned gently and sufficiently slowly.

After about five to six rotations, which corresponds to only a few, especially only up to four, rotation intervals of the brush attachment with actuation time about 10 s (seconds), detachment of the tick's body or the anchored puncturing apparatus and removal of the virtually intact tick is achieved. Transfer of pathogens is reliably avoided even in the possible case that the tip of the puncturing/suction apparatus (hypostome) remains in the puncture site when the tick leaves the puncture site. What is essential is that, by means of the apparatus of the invention, especially by means of the brush attachment, possible "tick breakoff" above the puncturing/suction apparatus of the tick is reliably avoided.

The arrangement of the fibers (fiber arrangement) is preferably cylindrical on the outside. The fiber arrangement is particularly advantageously concentric, with the axial length of radially inner fibers being less than the axial length of radially outer fibers. In this way, the recess and/or depression for positioning of the tick's body projecting from the host's skin is/are produced or can be produced in a particularly suitable manner. The particularly advantageous frustoconical form or paraboloid form of the recess may, depending on the fiber thickness or cross-sectional fiber area and difference in length of the fibers of the radially adjacent (theoretical) circular lines on which the fibers are arranged concentrically as fiber rings, be in more or less stepped form in axial direction.

The fibers are suitably arranged on at least two (2), especially not more than ten (10), preferably two (2) to six (6), further preferably three (3) to five (5), concentric circular lines or fiber rings. In this way, it is possible to provide brush attachments of different size, for example a small brush attachment with three fiber rings and a middle brush attachment with four fiber rings and a large brush attachment with five fiber rings.

In an advantageous configuration of the fibers, these have a triangular cross-sectional form. It has been found to be particularly effective when a triangular tip of the fibers is oriented radially outward. Moreover, it is particularly advantageous when the opposite side of the triangle from the triangular tip is indented (curved) in the form of a circular arc (concavely). In this way, it is possible to arrange the fibers of the respective fiber ring in a directly adjoining manner by their triangular side in the form of a circular arc to form a very exact circular form in circumferential direction. Furthermore, it has been found to be effective that the free end of the fiber of each or every fiber ends in a fiber tip. It is also advantageous when the arrangement of the fibers (fiber arrangement) on the external circumference of the free ends of the fibers has a taper directed radially inward.

The external diameter of the arrangement of the fibers, i.e. of the brush attachment in the region of the fiber arrangement, is greater than 1 mm, especially not less than 2 mm, and less than 20 mm, especially less than 10 mm, preferably not more than 7 mm, suitably (6±3) mm. The axial length of the attachment with the fibers (brush attachment length) is greater than 10 mm and less than 60 mm, especially between 20 mm and 50 mm, preferably (34±6) mm.

In order to specifically position the brush attachment on the parasite or on the tick in the handling of the device and to position the parasite's or tick's body reliably in the recess (depression) of the brush attachment, preferably as centrally as possible, a centering sleeve, especially a transparent centering sleeve, that surrounds the fiber arrangement is provided. This suitably consists of plastic. The centering sleeve is preferably fitted onto the housing in a removable manner, with the centering sleeve appropriately concluding (flush) with the free ends of the fibers of the brush attachment. By means of the centering sleeve, in addition, a specific fitting force of the brush attachment onto its positioning site is established, and hence unwanted compressive force on the tick in the course of its removal from the host's skin is reliably avoided.

Advantageously, a range comprising a number of brush attachments of different size is provided for the and/or with the device. This range with, for example, three brush attachments of different size (large, medium, small) may be accommodated in a receiving chamber (brush chamber) of the housing. The brush attachment may in principle also be used manually for removal of an acarine parasite that has penetrated into a host's skin, especially a tick.

It is also particularly advantageous to use a brush produced as a one-piece injection molding with a fiber arrangement that has a recess, preferably a coaxial recess, especially in conical or frustoconical or paraboloid form, for removing ticks from a host's skin by means of a compressive force-free, especially grip-free, rotating motion of the brush.

Other features which are considered as characteristic for the invention are set forth in the appended claims.

Although the invention is illustrated and described herein as embodied in a device for removing acarine parasites by rotation, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
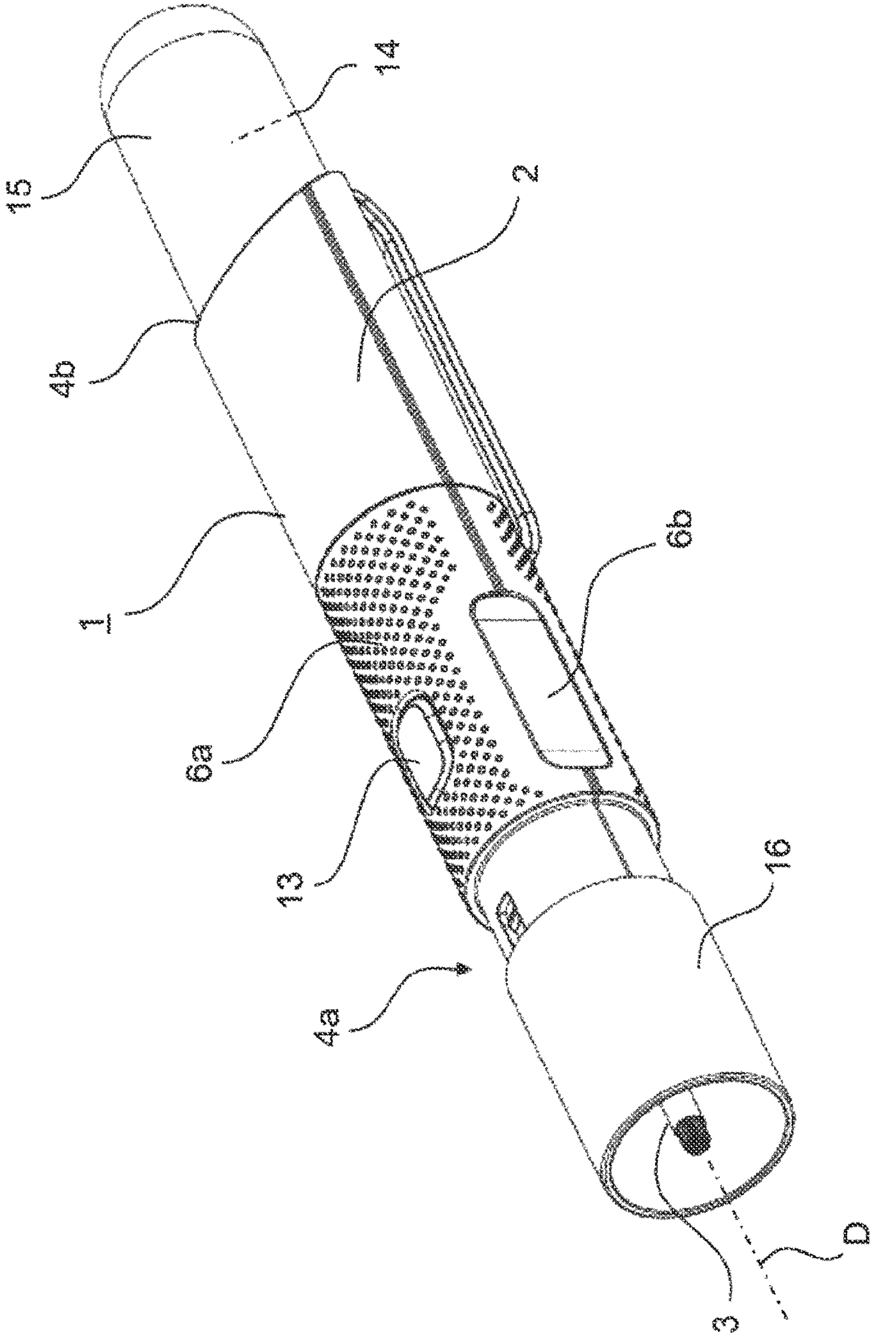
FIG. 1 is a diagrammatic, perspective view of a device provided and set up for removal of a tick that has penetrated into a host's skin, having a housing and having a rotor-driven (-drivable) attachment having a number of fibers arranged in the manner of a brush or bristles (brush attachment)

Mutually corresponding parts and parameters are given the same reference numerals in all figures.

Figure 2:
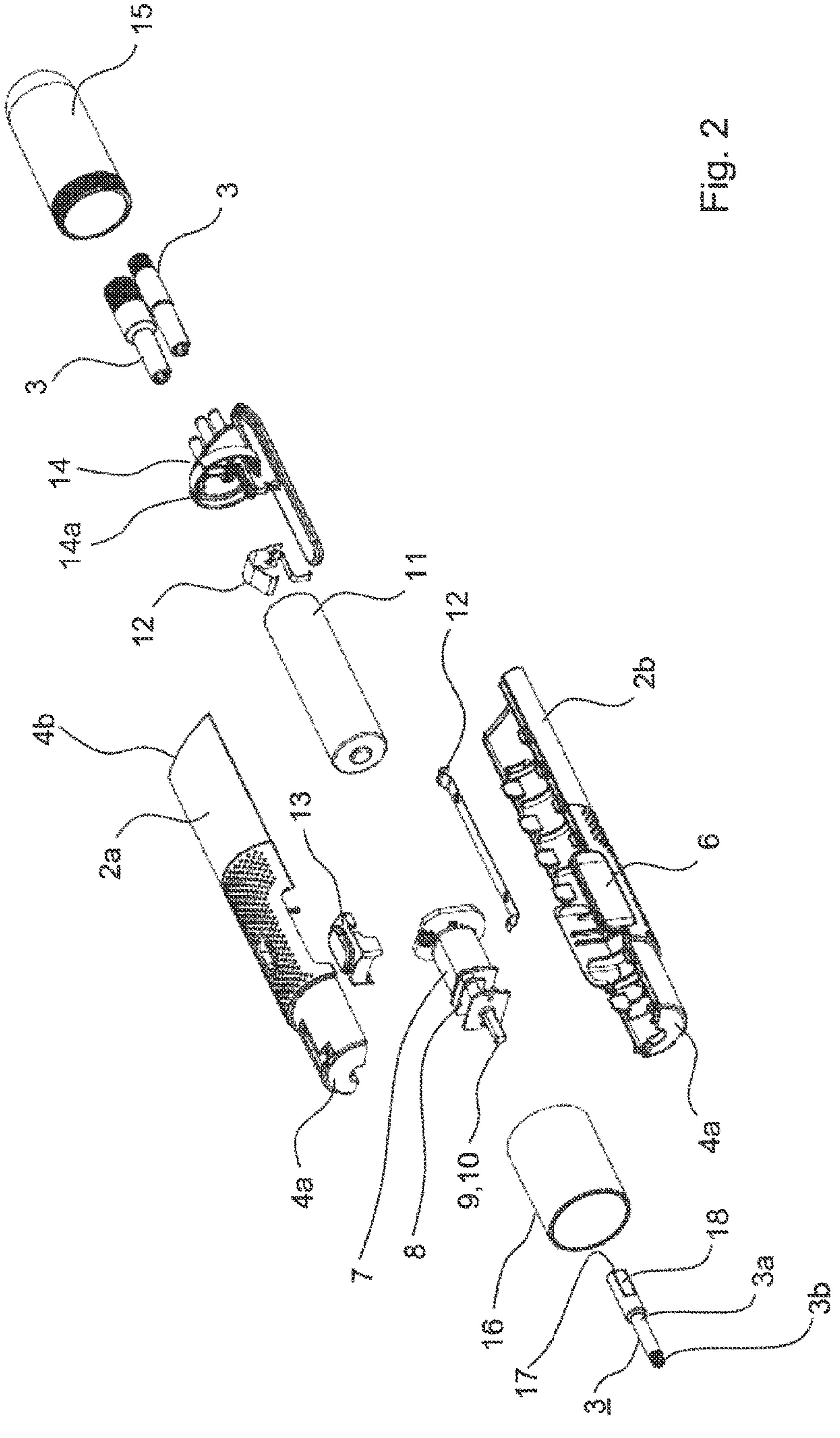
FIG. 2 is an exploded, perspective view of the apparatus according to FIG. 1.

Referring now to the figures of the drawings in detail and first, particularly to FIGS. 1-2 thereof, there is shown a device 1 that serves to remove an acarine parasite that has penetrated into a host's skin, especially a tick, and has a housing 2 and a brush attachment 3 releasably coupled at a (front) housing end face 4*a* to a drive 5 accommodated in the housing 2. The housing 2 is cylindrical and contains a grip surface with opposite recessed grips 6 for reliable handling of the device 1. The exchangeable brush attachment 3 coupled to the drive 5 is rotor-drivable or -driven about an axis of rotation D.

The drive 5 contains an electric motor 7 and a reduction gear 8, and also a drive shaft 9 to which the brush attachment 3 can be fitted or is fitted in a fixed manner at the end of the shaft. The drive shaft 9 thus forms a mechanical interface 10 for the brush attachment 3 at the housing end face 4*a*. An energy storage device 11 accommodated in the housing 2, especially one that is rechargeable, in the form of a battery or an accumulator, serves for power supply or supply of current to the electric motor 7 and hence for operation of the drive 5. For this purpose, contact pieces 12 within the housing are provided for electrical connection of the energy storage device 11 to the electric motor 8. The drive 5 may be switchable on and off by means of a switch or button 13 accessible from the outside. Preference is given to providing a button 13 with timer functionality. Particular preference is given to a switch-on time between 5 s (seconds) and 100 s, appropriately 5 s and 25 s. This is followed by automatic switch-off of the drive 5.

The housing 2 in the working example is executed in twin-shell form with an upper shell 2*a* and with a lower shell 2*b*. At the (rear) housing end face 4*b* of the housing 2 that is opposite the front end face 4*a* with the interface 11, the housing is provided with a receiving chamber (brush chamber) 14 with a chamber insert 14*a* for storage of brush attachments 3 of different size. A cap (screw cap) 15 releasably connected to the housing 2, especially screwed onto it, covers the receiving chamber 14. The cap 15 has an outer thread, and the housing 2 a corresponding inner thread. The effect of the cap 15, by means of the screw thread, is to exert an axial compressive force on the chamber insert 14*a* and via the latter the necessary contact force for the contacting of the contact elements 12 with the energy storage device 11. With the cap 15 removed, the chamber insert 14*a* can be taken out, such that the energy storage device 11 and/or the contact elements 12 can be removed from the housing 2.

At the front end face 4*a*, a preferably transparent centering sleeve 16 can be fitted or is fitted onto the housing 2. This ends flush with the brush attachment 3 at the free end.

By means of the reduction of the drive 5, a speed of the brush attachment 3 of especially (60±10) rpm or, for example, (120±10) rpm is established. The drive 5 may also be set up for a stepwise or continuous adjustment of speed.

The brush attachment 3 is a one-piece, i.e. one-part or monolithic, injection molding made of plastic. In other words, the brush attachment 3 is an attachment 3*a* having molded-on fibers in a brush-like arrangement, referred to hereinafter as fiber arrangement 3*b*. The rotor-driven fiber arrangement 3*b* is particularly suitable and advantageous for removal of ticks from a host's skin. The attachment 3*a* of the brush attachment 3 forms the mechanical interface 10 for the or to the drive 5. For this purpose, the attachment 5 has a shaft mount 17 open at the end, preferably with a flattened surface 18, for fixed coupling to the drive shaft 10. In a kinematic reversal, it is also possible for the drive shaft 10 to have the receptacle for a corresponding adapter of the attachment 3*b* at the end of the shaft. The attachment 3*b* is suitably clamp-fastened in a fixed and releasable manner to the drive shaft 10.

Figure 3A:
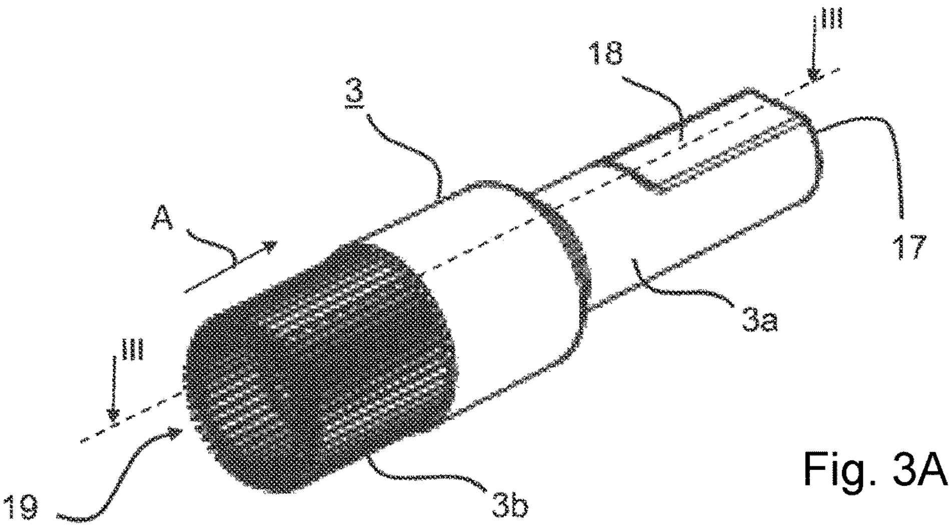
FIG. 3A is a perspective view of the brush attachment in a first variant (large) of a concentric fiber arrangement of the brush attachment.
Figure 3B:
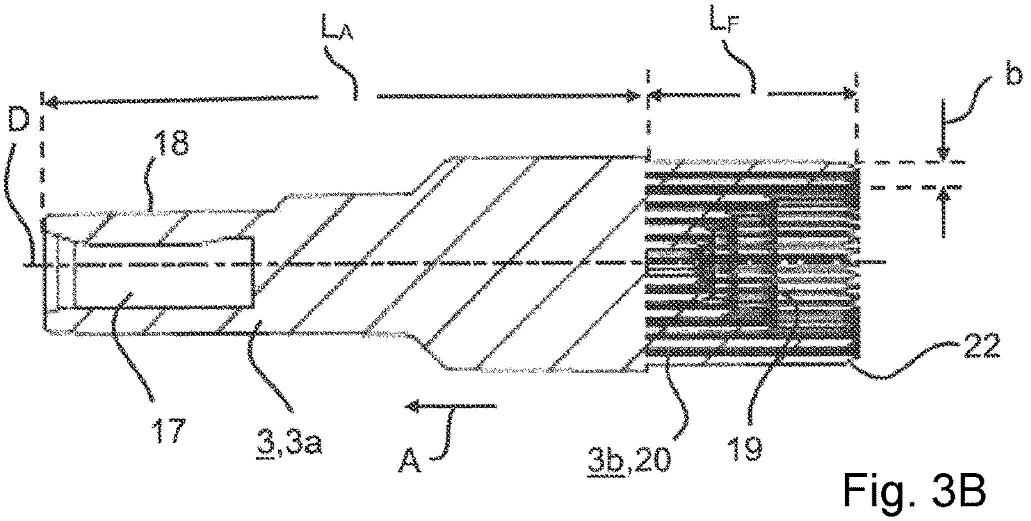
FIG. 3B is a sectional view taken along the line IIIB-IIIB shown in in FIG. 3A of the brush attachment in the first variant (large) of the concentric fiber arrangement of the brush attachment.
Figure 3C:
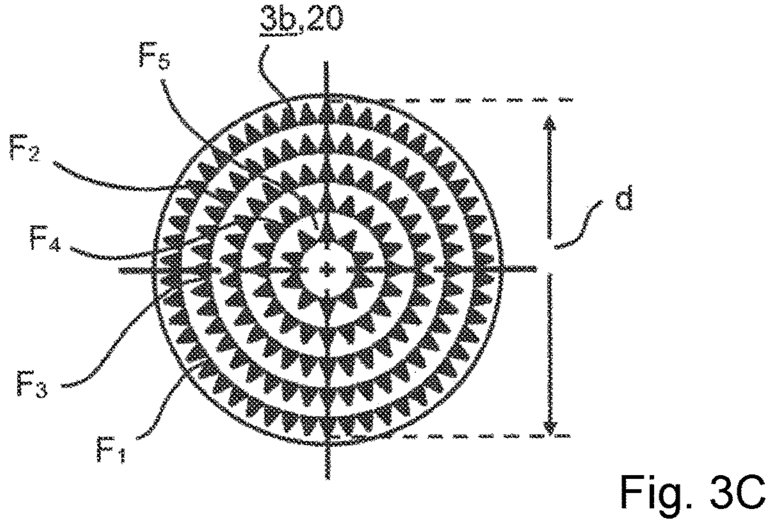
FIG. 3C is a top view of the brush attachment in a first variant (large) of the concentric fiber arrangement of the brush attachment.

FIGS. 3A to 3C show the brush attachment 3 in a first variant (large), preferably for a fully grown tick, in perspective view (FIG. 3A) and in a section view (FIG. 3B) along the line IIIB-IIIB shown in FIG. 3A, and in a top view (from the end face) of the preferably concentric fiber arrangement 3*a* (FIG. 3C).

The fiber arrangement 3*a* is cylindrical (at the outer circumference) and circular in cross section. The fiber arrangement 3*a* has a coaxial recess (depression) 19. This extends axially proceeding from the free end of the fibers of the fiber arrangement 3*b* along the axis of rotation D, and tapers in the direction of the axis of rotation D in the axial direction A shown. The recess 19 serves to accommodate a parasite's or tick's body in that the brush attachment 3 with the recess (depression) 19 is placed over the tick's body that projects out of the host's skin, such that it is covered in the manner of a hood and is accommodated in the recess 19.

The fiber arrangement 3*a* is concentric, with the axial length of inner fibers being less than the axial length of radially outer fibers. In other words, the fibers of different fiber length form the recess 19 for positioning of the parasite's or tick's body projecting out of the host's skin. The advantageous frustoconical or paraboloid form of the recess 19, depending on the fiber thickness or cross-sectional fiber area and the difference in length of the fibers of the radially adjacent (theoretical) circular lines on which the fibers are each in a radially spaced arrangement as fiber rings $F_n$ (FIGS. 3 to 5), is stepped to a greater or lesser degree in axial direction A.

The recess 19 has the function of enclosing the tick's body in the manner of a hood by means of the fiber arrangement 3*b* of the brush attachment 3 without compressing, squeezing or injuring the tick's body, such that the tick within the recess 19 in the fiber arrangement 3*b* of the brush attachment 3 can rotate with the rotation with the tick's legs meshed and with the machine or device 1 switched on.

The fibers of the brush attachment 3 according to FIGS. 3A to 3C are arranged in five concentric (theoretical) circular lines, each of which forms a fiber ring $F_n$. The diameter d of the outer fiber ring $F_1$ of the fiber arrangement 3*b* in the working example is t=(7.2±0.2) mm. The circle diameter on which the fibers lie alongside one another here is 7 mm. The otherwise unspecified diameters of the fiber rings $F_2$ to $F_5$ that follow in the radially inward direction are each about 1.4 mm less in the working example from radially outward to radially in each case. The circle diameter on which these fibers lie alongside one another is between 1.4 mm and 5.6 mm.

The axial length $L_A$ of the attachment is about 23 mm. The axial length $L_F$ of the fibers or fiber rings in this working example is about 8 mm for the first outer and second fiber rings $F_1$ and $F_2$, about 5.0 mm for the third fiber ring $F_3$, about 3.5 mm for the fourth fiber ring $F_4$, and about 2.5 mm for the fifth fiber ring $F_5$. The two fiber rings $F_1$ and $F_2$ form a fiber ring arrangement $F_{12}$, the (radial) ring width b of which is suitably (1.0±0.2) mm.

Figure 4A:
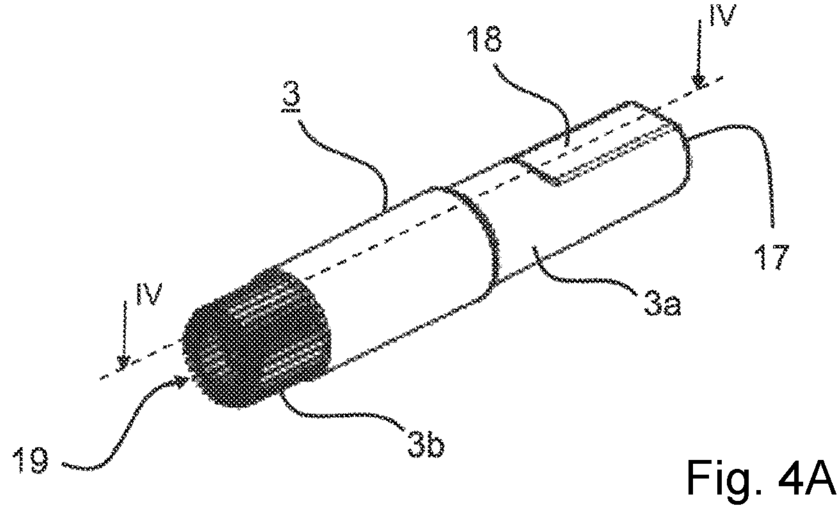
FIG. 4A is a perspective view of the brush attachment in a second variant of the concentric fiber arrangement of a medium-sized brush attachment.
Figure 4B:
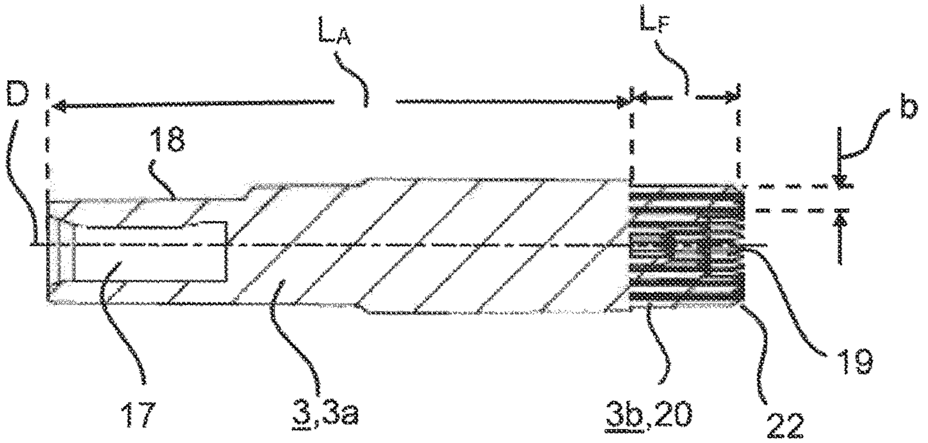
FIG. 4B is a sectional view taken along the line IVB-IVB shown in FIG. 4A of the brush attachment in the second variant (middle) of the concentric fiber arrangement of the medium-sized brush attachment.
Figure 4C:
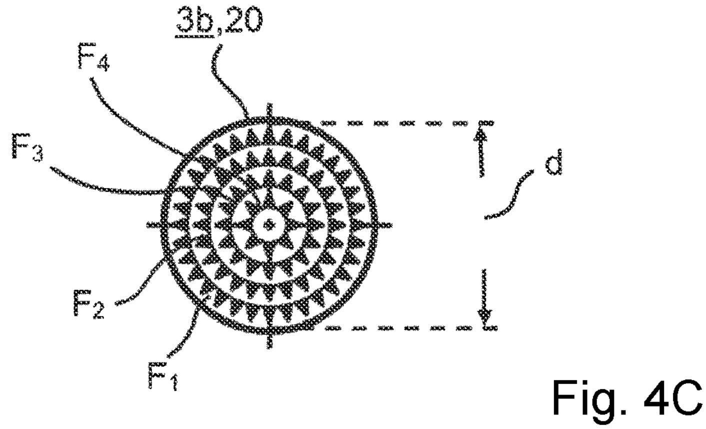
FIG. 4C is a top view of the brush attachment in the second variant (middle) of the concentric fiber arrangement of the medium-sized brush attachment.

FIGS. 4A to 4C show the brush attachment 3 in a second variant (middle), preferably for a nymph, in perspective view (FIG. 4A) and in a section view (FIG. 4B) along the line IVB-IVB in FIG. 4A, and in a top view (of the end) of the preferably concentric fiber arrangement 3*a* (FIG. 4C).

The fibers of the brush attachment 3 according to FIGS. 4A and 4B are arranged on four concentric (theoretical) circular lines that each in turn form a fiber ring $F_n$. The diameter d of the outer fiber ring $F_1$ of the fiber arrangement 3*b* in this working example of the medium-sized brush attachment 3 is about (4.6±0.2) mm. The external diameter of the fiber rings $F_2$ to $F_4$ that follow in radially inward direction, in the working example, are each about 1.2 mm smaller in turn from the radially outward to radially inward direction. The two outer fiber rings $F_1$ and $F_2$ again form the fiber ring arrangement $F_{12}$.

The axial length $L_A$ of the attachment is about 26 mm. The axial length $L_F$ of the fibers or fiber rings $F_n$ on these circular lines in this working example is about 5 mm for the first outer and second fiber rings $F_1$, $F_2$, about 3.5 mm for the third fiber ring $F_3$, and about 1.9 mm for the fourth fiber ring $F_4$. The (radial) ring width b of the two outer fiber rings $F_1$ and $F_2$ that form the fiber ring arrangement $F_{12}$ is again suitably (1.0±0.1).

Figure 5A:
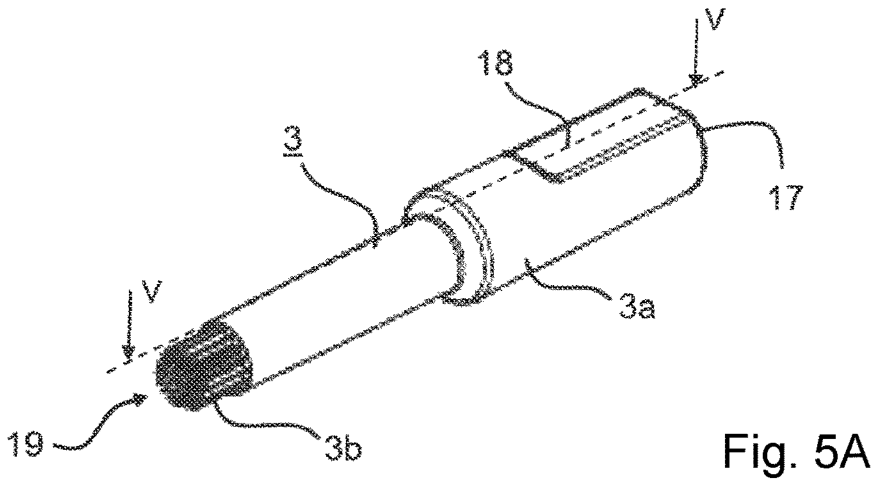
FIG. 5A is a perspective view of the brush attachment in a third variant (small) of the concentric fiber arrangement of the small-sized brush attachment.
Figure 5B:
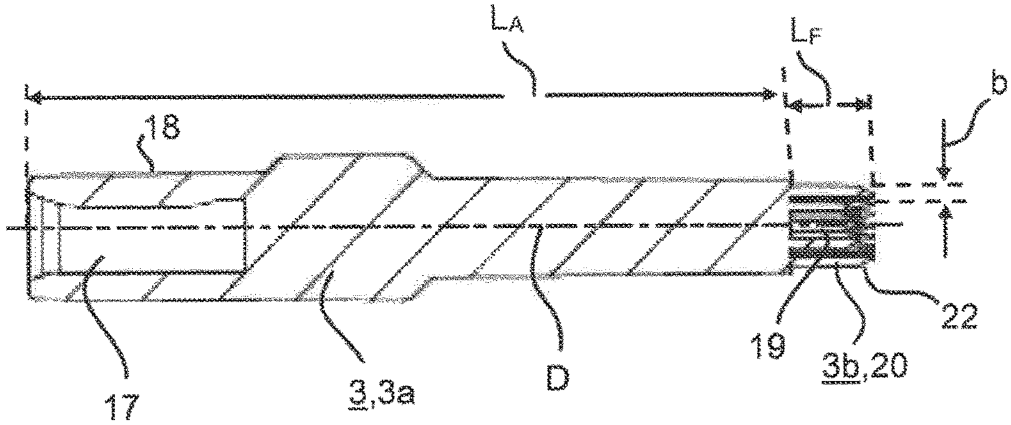
FIG. 5B is a sectional view of the brush attachment in the third variant (small) taken along the line VB-VB shown in FIG. 5A of the centric fiber arrangement of the small-sized brush attachment.
Figure 5C:
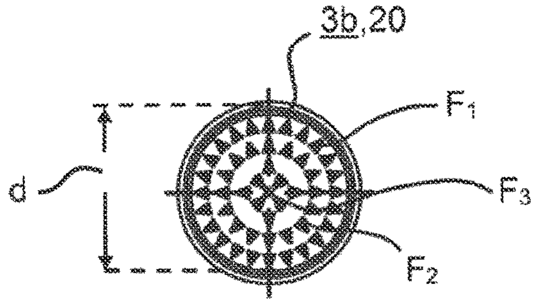
FIG. 5C is a top view of the brush attachment in the third variant (small) of the concentric fiber arrangement of the small-sized brush attachment.

FIGS. 5A to 5C show the brush attachment 3 in a third variant (small), preferably for a larva, in perspective view (FIG. 5A) and in a section view (FIG. 5B) along the line VB-VB in FIG. 5A and in a top view (of the end) of the preferably concentric fiber arrangement 3*a* (FIG. 5C).

The fibers of the brush attachment 3 according to FIGS. 5A to 5B are arranged on three concentric (theoretical) circular lines, each of which again forms a fiber ring $F_n$. The diameter d of the outer fiber ring $F_1$ of the fiber ring arrangement 3*b* in this working example of the small-sized brush attachment 3 is about 3.6 mm. The external diameter of the fiber rings $F_2$ and $F_3$ that follow in radially inward direction, in the working example, are each about 1.2 mm smaller in turn. The (radial) ring width b of the two outer fiber rings $F_1$ and $F_2$ that form the fiber ring arrangement $F_{12}$ is again suitably (1.0±0.1) mm.

The axial length $L_A$ of the attachment in this working example is about 28 mm. The axial length $L_F$ of the fibers of the outer fiber ring $F_1$ is 3 mm. The axial length of the fibers of the inner fiber ring $F_3$ that is concentric thereto and has triangle tips directed alternately outward and inward is about 2.8 for the fibers with triangle tips directed outward and 2.5 mm for the fibers with triangle tips directed inward.

Figure 6:
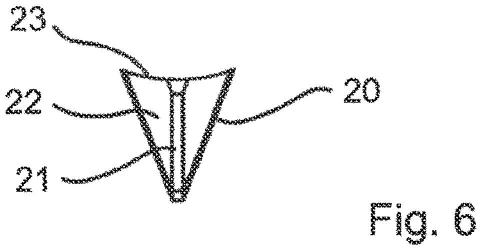
FIG. 6 a large-scale view of a single fiber of the brush attachment, looking at a fiber tip.

As shown in FIG. 6 by an individual fiber 20 of the brush attachment 3, the fibers are triangular in cross section. One of the triangle tips of the fibers 20 is oriented radially outward. Only in the embodiment according to FIGS. 5A to 5C are the triangle tips of the fibers of the inner fiber ring $F_3$ directed alternately inward and outward in circumferential direction.

The free end of the fiber 20 at least of the outer fiber ring $F_1$ ends in a fiber tip 21. It is advantageous here that the fiber tips 21 have a slope 22 running radially inward, such that the fiber arrangement 3*b*, at the outer circumference of the free ends of the fibers—i.e. at the free ends of the fibers—has a taper directed radially inwards formed by the slopes 22. What this achieves is that, when the fiber arrangement 3*b* of the brush attachment 3 is fitted, the free ends of the fibers, in the case of appropriate axial exertion of pressure on the host's skin, preferentially give way in the inward direction (radially inward) and are less likely to give way in the (radially) outward direction. This advantageously improves the efficacy of the device 1 in the removal of the tick that has penetrated into the host's skin.

The width or thickness of an (individual) fiber 20 (beneath the fiber tip 21) is preferably 0.3 mm to 0.4 mm, for example about 0.34 mm at the narrowest site and about 0.4 mm at the broadest site. The side of the triangle 23 opposite the fiber tip 21 is curved inward in the form of a circular arc. In the arrangement of the fibers 20 to give the circular ring $F_n$, this achieves a very exact circular shape. The fiber rings $F_n$ are suitably spaced apart from one another, with the radial distance between adjacent fiber rings $F_n$ being about 0.1 mm to 0.4 mm, preferably 0.2 mm to 0.3 mm.

By means of the device 1, even after a few rotations of the brush attachment 3 rotor-driven about the axis of rotation D, achieves the effect that the tick detaches its puncture apparatus from the host's skin and leaves the puncture site. The coaxial recess 19 that tapers axially achieves the effect here that the fibers move between the extremities of the tick (the tick's legs). This enables the desired rotary movement of the tick within the puncture site and ensures reliable parting of the tick from the puncture site. The tick is removed here from the host's skin in a particularly simple and reliable manner and especially virtually without destruction, and the detached tick is then in the recess 19 of the brush attachment 3.

In the handling of the device 1, the brush attachment 3 and especially its fiber arrangement 3*b* with the recess 19, by means of the transparent centering sleeve 16, are positioned exactly over the tick in order to position the tick's body with certainty in the recess 19 of the brush attachment 3. The centering sleeve 16 fitted onto the housing 2 ends flush with the free fiber ends of the brush attachment 3 or is slightly axially offset with respect to the latter. The centering sleeve 16 may be fitted on the housing 2 in a removable manner. The centering sleeve 16 is preferably disposed on the housing 2 such that it cannot be lost, and is appropriately movable axially thereon, it being possible for the centering sleeve 16 to be latched in the forward position shown and/or in a withdrawn position.

The cylindrical centering sleeve 16 has a diameter of 9 mm to 30 mm, preferably (20±5) mm. The function thereof is firstly to provide a protective shell for the brush attachment 3 in order to avoid unnecessary wear or unwanted bending of the brush attachment 3. Secondly, it is ensured that a user, by virtue of the fitting of the centering sleeve 16 on the skin, is able to implement reliable use within the circumference around the tick centered in the middle by means of the sleeve circle. More particularly, by means of the centering sleeve 16, it is possible to establish a controlled minimum fitting pressure of the brush attachment 3 to the host's skin. Therefore, the centering sleeve 16 should conclude at the front (end) very exactly with the free ends of the fibers, such that the fiber arrangement 3*b* and the centering sleeve 16 are in simultaneous contact with the skin. Moreover, the centering sleeve 16 prevents the tick from falling downward after release.

The device 1, on utilization thereof, especially at parts of the body that are difficult to access, can be employed without or with the centering sleeve 16 retracted axially. After utilization, the brush attachment 3 should be cleaned, disinfected, or exchanged if necessary.

In summary, the invention relates to a device 1 for removing an acarine parasite that has penetrated into a host's skin, having a drive 5 accommodated in a housing 2 and an attachment 3, 3*a* that is rotatable about an axis of rotation and has a brush-like fiber arrangement 3*b* having a recess 19, wherein a fiber ring arrangement $F_{12}$ formed by the fibers at their free ends along the circumference of the recess 19 has a ring with b between 0.3 mm and 1.4 mm, especially (0.8±0.4) mm. In a particularly advantageous configuration, the attachment 3*a* together with the fibers or with the fiber arrangement 3*b*—i.e. the brush attachment 3—forms a one-piece injection molding, especially made of plastic.

The invention claimed is not limited to the working examples described above. Instead, other variants of the invention can also be derived therefrom by the person skilled in the art within the scope of the claims disclosed without leaving the subject-matter of the invention claimed. More particularly, in addition, all individual features described in connection with the various working examples, within the scope of the claims disclosed, are also combinable in other ways within the scope of the claims disclosed without leaving the subject-matter of the invention claimed. For instance, the brush attachment can also—effectively as a brush—be used manually to remove an acarine parasite that has penetrated into a host's skin, especially a tick.

The following is a summary list of reference numerals and the corresponding structure used in the above description of the invention:

1 device
2 housing
2*a* upper shell
2*b* lower shell
3 brush attachment
3*a* attachment
3*b* fiber arrangement
4*a* (forward) housing end face
4*b* (rear) housing end face
5 drive
6*a* grip surface
6*b* recessed grip
8 electric motor
8 reduction gear
9 drive shaft
10 interface
11 energy storage means
12 contact element/piece
13 switch/button
14 receiving chamber
14*a* chamber insert
15 cap
16 centering sleeve
17 shaft mount
17 flattened surface
19 recess/depression
20 fiber
21 fiber tip
22 slope/taper
A axial direction
$F_n$ fiber ring
D axis of rotation
b ring width
d diameter
$L_A$ attachment length
$L_F$ fiber length

The invention claimed is:

1. A device for removing an acarine parasite that has penetrated into skin of a host, the device comprising:
a housing;
a drive accommodated in said housing and having on a drive side an interface; and
an attachment being rotatable about an axis of rotation and having a plurality of fibers disposed in a manner of a brush as a fiber ring configuration, wherein said fiber ring configuration having a recess formed therein, wherein said fibers forming said fiber ring configuration at free ends of said fibers along a circumference of said recess and said fiber ring configuration having at least one fiber ring with a ring width of not less than 0.3 mm but less than 1.5 mm, the ring width being half a difference between an outer dimension and an inner dimension of said at least one fiber ring at a mouth of said recess at said free ends of said fibers forming said at least one fiber ring.

2. The device according to claim 1, wherein:
said fiber ring configuration is formed from two fiber rings, the ring width of which is between 0.4 mm and 1.2 mm.

3. The device according to claim 2, wherein:
the ring width is not more than 1.4 mm; and/or
said fiber ring configuration having said two fiber rings has the ring width being 1.0±0.2 mm.

4. The device according to claim 1, wherein said attachment together with said fiber configuration is a one-piece injection molding.

5. The device according to claim 1, wherein said fiber configuration is concentric, with an axial length of inner fibers of said fibers being shorter than an axial length of radially outer fibers of said fibers.

6. The device according to claim 1, wherein said fibers are disposed in at least two concentric fiber rings.

7. The device according to claim 1, wherein:
said fibers have a triangular fiber cross section.

8. The device according to claim 7, wherein in said triangular fiber cross section, a triangular tip of said fibers is oriented radially outward.

9. The device according to claim 1, wherein said fiber ring configuration has a taper directed radially inward at an outer circumference of said free ends of said fibers.

10. The device according to claim 1, wherein an external diameter of said fiber ring configuration is greater than 1 mm.

11. The device according to claim 1, wherein:

a length of said attachment with said fiber ring configuration is greater than 10 mm and less than 60 mm; and/or said length of said fiber ring configuration is greater than 1.5 mm and less than 30 mm.

12. The device according to claim 1, further comprising a centering sleeve surrounding said fiber ring configuration and fitted onto said housing, said centering sleeve ends flush with said free ends of said fibers of said attachment.

13. The device according to claim 1, wherein said drive has a drive shaft that forms said interface and by said interface said attachment can be fitted to said fiber ring configuration in a fixed manner at an end of said drive shaft, said interface being a mechanical interface.

14. The device according to claim 1, wherein said drive has an electric motor and a reduction gear with a reduction being set such that a speed of said attachment with said fiber ring configuration being between 30 rpm and 150 rpm.

15. The device according to claim 1, wherein:

the device is configured for removing ticks;

said drive is an electric motor drive;

said recess is a coaxial recess in conical, frustoconical or paraboloid form; and said ring width is 0.8±0.4 mm.

16. The device according to claim 1, wherein said fibers are disposed in 2 to 6 concentric fiber rings.

17. The device according to claim 1, wherein an external diameter of said fiber ring configuration is not less than 2 mm and less than 10 mm.

18. A brush attachment, comprising:

a plurality of concentrically disposed fibers or fiber rings for removal of an acarine parasite that has penetrated into skin of a host for the device according to claim 1.

19. A range, comprising:

a plurality of brush attachments of different size for the device according to claim 1.

* * * * *